(12) United States Patent
Zhou et al.

(10) Patent No.: US 7,833,369 B2
(45) Date of Patent: Nov. 16, 2010

(54) STRAND, SUBSTRATE, AND/OR COMPOSITE COMPRISING RE-ACTIVATABLE ADHESIVE COMPOSITION, AND PROCESSES FOR MAKING AND/OR UTILIZING SAME

(75) Inventors: Peiguang Zhou, Appleton, WI (US); Gregory K. Hall, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1298 days.

(21) Appl. No.: 11/302,756

(22) Filed: Dec. 14, 2005

(65) Prior Publication Data

US 2007/0131335 A1  Jun. 14, 2007

(51) Int. Cl.
*B32B 37/00* (2006.01)
(52) U.S. Cl. ............... 156/73.1; 156/164; 156/229; 156/290
(58) Field of Classification Search ......... 156/73.1, 156/73.2, 160, 161, 163, 164, 229, 290, 291, 156/308.2, 308.4, 580.1
See application file for complete search history.

(56) References Cited

U.S. PATENT DOCUMENTS

| 3,338,992 | A | 8/1967 | Kinney |
| 3,341,394 | A | 9/1967 | Kinney |
| 3,366,115 | A | 1/1968 | Champaigne, Jr. |
| 3,502,538 | A | 3/1970 | Petersen |
| 3,502,763 | A | 3/1970 | Hartmann |
| 3,542,615 | A | 11/1970 | Dobo et al. |
| 3,692,618 | A | 9/1972 | Dorschner et al. |
| 3,733,238 | A | 5/1973 | Long et al. |
| 3,802,817 | A | 4/1974 | Matsuki et al. |

(Continued)

FOREIGN PATENT DOCUMENTS

DE  26 49 948 A1  5/1977

(Continued)

OTHER PUBLICATIONS

American Society for Testing Materials (ASTM) Designation: E 28-97, "Standard Test Methods for Softening Point of Resins by Ring-and-Ball Apparatus," pp. 678-684, published Sep. 1997.

*Primary Examiner*—James Sells
(74) *Attorney, Agent, or Firm*—John L. Broderson (57) ABSTRACT

The present invention is generally directed to webs, components, composites, and strands comprising re-activatable adhesive compositions, as well as health-and-hygiene products employing such webs, components, composites, and strands. By inputting energy to the web, component, composite, or strand (including, for example, an elastic web, component, composite, or strand) comprising a re-activatable adhesive composition, the adhesive is activated (i.e., rendered tacky) so that it can be used to join or adhere the web, component, composite, or strand to another material (or another location on the same web, component, composite, or strand). Generally, energy will be inputted to the adhesive in the form of infrared heat, heat, or ultrasonic energy, although any energy form may be used, so long as the energy is capable of activating the adhesive. Prior to activation, webs, components, composites, and strands comprising such re-activatable adhesives are convenient to handle because the adhesive is not yet tacky. Furthermore, the re-activatable adhesive may be activated at desired locations only, thereby permitting construction of bond patterns that promote desired characteristics (e.g., desired ratios of elastic properties and softness).

32 Claims, 5 Drawing Sheets

U.S. PATENT DOCUMENTS

| | | |
|---|---|---|
| 3,849,241 A | 11/1974 | Butin et al. |
| 4,081,301 A | 3/1978 | Buell |
| 4,340,563 A | 7/1982 | Appel et al. |
| 4,519,798 A | 5/1985 | Dinius |
| 4,610,681 A | 9/1986 | Strohbeen et al. |
| 4,641,381 A | 2/1987 | Heran et al. |
| 4,798,603 A | 1/1989 | Meyer et al. |
| 4,823,783 A | 4/1989 | Willhite, Jr. et al. |
| 4,919,738 A | 4/1990 | Ball et al. |
| 4,940,464 A | 7/1990 | Van Gompel et al. |
| 5,176,668 A | 1/1993 | Bernardin |
| 5,176,672 A | 1/1993 | Bruemmer et al. |
| 5,192,606 A | 3/1993 | Proxmire et al. |
| 5,213,881 A | 5/1993 | Timmons et al. |
| 5,902,297 A | 5/1999 | Sauer |
| 5,904,672 A | 5/1999 | Lemahieu et al. |
| 5,904,675 A | 5/1999 | Laux et al. |
| 6,248,195 B1 | 6/2001 | Schmitz |
| 2002/0123538 A1 | 9/2002 | Zhou et al. |
| 2002/0157778 A1* | 10/2002 | Sorenson et al. ............ 156/264 |
| 2004/0163754 A1 | 8/2004 | Nowicki et al. |

FOREIGN PATENT DOCUMENTS

| | | |
|---|---|---|
| GB | 2 054 350 A | 2/1981 |
| WO | WO 82/00307 A1 | 2/1982 |
| WO | WO 99/25296 A1 | 5/1999 |

* cited by examiner

STRAND, SUBSTRATE, AND/OR COMPOSITE COMPRISING RE-ACTIVATABLE ADHESIVE COMPOSITION, AND PROCESSES FOR MAKING AND/OR UTILIZING SAME

BACKGROUND

People rely on health and hygiene products to make their lives easier.

Health and hygiene products, such as various disposable absorbent articles (e.g., adult incontinence articles and diapers), are generally manufactured by combining several components. These components may include, for example, a liquid-permeable topsheet; a liquid-impermeable backsheet attached to the topsheet; and an absorbent core located between the topsheet and the backsheet. When the disposable article is worn, the liquid-permeable topsheet is positioned next to the body of the wearer. The topsheet allows passage of bodily fluids into the absorbent core. The liquid-impermeable backsheet helps prevent leakage of fluids held in the absorbent core. The absorbent core generally is designed to have desirable physical properties, e.g. a high absorbent capacity and high absorption rate, so that bodily fluids can be transported from the skin of the wearer into the disposable absorbent article.

Frequently one or more components of a health-and-hygiene article are adhesively bonded together. For example, adhesives have been used to bond individual layers of an absorbent article, such as the topsheet (also known as, for example, the body-side liner) and backsheet (also known as, for example, the outer cover), together. Adhesive has also been used to bond discrete pieces, such as fasteners and leg elastics, to the article. In many cases, the bonding together of components forms a laminated structure in which adhesive is sandwiched between materials (such as layers of polymer film and/or layers of woven or nonwoven fabrics) that make up the components being bonded together. In some cases elastic strand, or some other elastomeric material, is attached to and/or sandwiched between other components.

In many instances, a hot-melt adhesive, i.e. a formulation that is heated to substantially liquefy the formulation prior to application to one or both materials when making a laminate, is used in making a laminated structure. While such formulations generally work, they can be improved upon. For example, in making some elastomeric composites, the add-on rate of the adhesive may be relatively high, resulting in a relatively costly, and somewhat rough or stiff, composite. E.g., the production of an elastomeric composite comprising one or more elastic strands sandwiched between, and adhesively attached to, nonwoven substrates (or facings) may require significant amounts of adhesive to ensure that the strands are satisfactorily attached to the nonwoven facings, thereby giving the composite its elastomeric qualities. At every location where a strand is adhesively attached to one or both facings, the composite is stiffer, because the combination of the strand, nonwoven facing, and adhesive is thicker and stiffer than either the strand alone or the nonwoven facing alone. If the composite comprises many such attachment locations, then the resulting composite may be stiff, rough, and/or perceived by users of the composite as not being soft. Furthermore, as the number of attachment locations is increased, the elastic qualities of the elastomeric composite may decrease, because more and more of the strand is attached to the nonwoven facings, with less and less of the strand remaining unattached. As less and less of the strand remains free and unattached—and therefore readily able to stretch or retract—the resulting composite is less stretchable and/or retractable. Conversely, as more and more of the strand remains free and unattached, the resulting composite is more stretchable and/or retractable.

The problem of achieving the desired balance between the integrity of an elastomeric laminate and effecting desired properties of softness/flexibility and elasticity may be exacerbated at the higher line speeds typically associated with commercial equipment (e.g., the equipment used to make a disposable absorbent article such as a diaper, which may operate at speeds, for example, of at least 300 feet per minute; suitably 500 feet per minute, particularly 750 feet per minute). As the line speed of the equipment increases, it typically becomes more and more difficult to intermittently attach an elastomeric material, such as elastic strand, to a substrate. For example, if the laminate is being made by attaching elastic strand to a substrate using a hot-melt adhesive applied through a nozzle, then intermittent bonding might be achieved by rapidly pulsing the adhesive (i.e., applying it in a discontinuous fashion). But at higher and higher line speeds, the pulsing of adhesive at higher and higher frequencies may be mechanically difficult. I.e., it may be difficult to produce the desired pattern of discrete bonding points between the elastic material and the substrate.

What is needed is a composite (e.g., an elastomeric composite), and method of making such a composite, that provides for one or more performance characteristics that are comparable to, or better than, one or more of the same performance characteristics (e.g., bond strength) of a conventional composite, while at the same time having improved softness characteristics. E.g., what is needed is a composite comprising elastomeric materials, such as elastomeric strands, attached to one or more substrates such that the composite has sufficient integrity, elasticity, and softness for use in a product.

SUMMARY

We have found that pre-treating one or more of the individual components that make up a composite with a re-activatable adhesive composition, and then making the composite by activating the adhesive composition on an individual component prior to attaching the component to itself or a second component, can provide for a softer, more flexible composite. Furthermore, such pre-treatment and re-activation can provide for desired intermittent and/or discrete bonding patterns between the components. So, for example, when bonding an elastomeric material, such as elastic strand, to a substrate, such pre-treatment of the substrate and/or strand with a re-activatable adhesive, followed by selectively inputting energy to the adhesive using ultrasonic equipment, can provide for precise bonding locations between the substrate and elastomeric material. The ability to effect relatively precise bonding locations allows for patterns of bonding locations that more properly balance strength/integrity, flexibility/softness, and elasticity in a desired way.

For example, in one representative version of the present invention, a re-activatable adhesive may be selected such that the adhesive possesses a lower softening point than the softening point (or, as discussed below, when the phase transition from liquid to solid is relatively sharp, melting point) material or component to which it will be applied. The component is then processed in a way such that the component is treated with the re-activatable adhesive. If the component is an elastic strand, a spool or bobbin of strand can be unwound such that the strand is directed continuously to a location where the re-activatable adhesive is applied by coating, spraying, printing, or otherwise treating the strand with the adhesive. Typically the re-activatable adhesive will have been heated to a temperature at or above its softening point so that the adhesive can be conducted to, and applied to, the component. Furthermore, by selecting an adhesive having a softening temperature lower than that of the component or substrate to which the adhesive is applied, there is decreased likelihood of the substrate itself losing integrity because of the substrate beginning to soften. After the re-activatable adhesive has been applied to a component, in this representative example an elastic strand, the adhesive is allowed to set (i.e., sufficient time is given for the temperature of the adhesive to decrease such that the adhesive hardens). The component treated with the re-activatable adhesive is then further processed (e.g., for immediate use in the making of an article of manufacture; or for storage prior to use for such manufacturing). For example, if the component is an elastic strand, and the strand is to be stored prior to its use in making a composite employed in an article of manufacture (such as a disposable absorbent article—e.g., a diaper, or some other health-and-hygiene product), then the strand treated with the re-activatable adhesive can be re-wound to form a spool or bobbin. When the spool of treated elastic strand is to be used (whether in the same location where the spool was treated; or at some other location different from the location where the spool was treated), the spool can be unwound, with the strand directed to one or more other components to which the strand will be attached. E.g., the strand could be directed to a position between two nonwoven substrates. Energy is directed to the re-activatable adhesive to activate its adhesive qualities. One method of directing energy to the re-activatable adhesive is by conducting the combination of the treated elastic strand and nonwoven facings through an ultrasonic unit operation. By directing the combination of these materials through ultrasonics equipment, ultrasonic energy is absorbed by the re-activatable adhesive. By selecting the amount of ultrasonic energy inputted to the combination; the identity of the re-activatable adhesive, particularly its softening point; the identity of the elastic strand, particularly its softening point; and the identity of the nonwoven facings, particularly their softening points; the adhesive can be activated such that its adhesive qualities are activated while maintaining the integrity of components of the combinations. I.e., these parameters may be selected such that the adhesive softens, flows, and adhesively attaches the strand to the nonwoven facings; while the components of the combination (the strand and the nonwoven facings) do not substantially soften or flow. Furthermore, the use of ultrasonic-bonding equipment provides the opportunity to adhesively bond the elastic strand to the nonwoven facings at discrete locations. As discussed generally above and elsewhere, the strand may be bonded intermittently along its length to other component(s), such as to one or both fibrous facings in an elastomeric laminate (i.e., the strands are sandwiched between, and attached to, the facings). If the strand is attached to the facings in this manner while in a stretched condition, then the resulting laminate, when allowed to retract (due to the strand retracting), will have elastomeric qualities. Energy may be inputted to activate the re-activatable adhesive either before, during, or after the component bearing the re-activatable adhesive is contacted with the component that is to be attached via the activated adhesive.

The preceding paragraphs provide a description of one representative version of the present invention. Additional detail is provided in the Description section that follows. Of course other versions and embodiments are possible. For example, rather than pre-treat an elastic strand with a re-activatable adhesive, nonwoven substrates of various types might be pre-treated. Any component employed in the making of an article of manufacture (e.g., a disposable absorbent article such as a diaper, or other health-and-hygiene product) can be pre-treated with a re-activatable adhesive such that during the making of the article of manufacture, energy is inputted to the adhesive such that it is activated and therefore capable of binding the pre-treated component either to itself or another component.

These and other features, aspects, and advantages of the present invention will become better understood with regard to the following description, appended claims, and accompanying drawings.

DESCRIPTION

The present invention is generally directed to re-activatable adhesive compositions, components employing such compositions, higher-order products made with these components, and processes for making said components and products. Composites employing re-activatable adhesive compositions generally perform better, and may cost less, than composites employing conventional hot-melt adhesives. Furthermore, these re-activatable adhesive compositions may typically be processed and applied using conventional hot-melt-adhesive processing equipment. Generally new equipment will not be necessary to use adhesive compositions of the present invention.

Before describing representative embodiments of the invention, it is useful to define a number of terms for purposes of this application. These definitions are provided to assist the reader of this document, and the presence or omission of specific terms should not be construed as evidence of knowledge possessed by persons of ordinary skill in the art or arts that relate to the subject matter of this document.

"Nonwoven" fabric or web means a web having a structure of individual fibers or threads that are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note: to convert from osy to gsm, multiply osy by 33.91.)

"Woven" fabric or web means a fabric or web containing a structure of fibers, filaments, or yarns, which are arranged in an orderly, inter-engaged fashion. Woven fabrics typically contain inter-engaged fibers in a "warp" and "fill" direction. The warp direction corresponds to the length of the fabric while the fill direction corresponds to the width of the fabric. Woven fabrics can be made, for example, on a variety of looms including, but not limited to, shuttle looms, rapier looms, projectile looms, air jet looms, and water jet looms.

"Spunbonded fibers", or "spunbond fibers", means small-diameter fibers that are typically formed by extruding molten thermoplastic material as filaments from a plurality of fine capillaries of a spinneret having a circular or other configuration, with the diameter of the extruded filaments then being rapidly reduced as by, for example, in U.S. Pat. No. 4,340,563 to Appel et al., and U.S. Pat. No. 3,692,618 to Dorschner et al, U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al., each of which is incorporated by reference in its entirety and in a manner consistent with the present document. Spunbond fibers are quenched and generally not tacky when they are deposited onto a collecting surface. Spunbond fibers are generally continuous and often have average diameters larger than about 7 microns, and more particularly between about 10 and 30 microns. A spunbond material, layer, or substrate comprises spunbonded (or spunbond) fibers.

The term "meltblown fibers" means fibers formed by extruding a molten material, typically thermoplastic in nature, through a plurality of fine, usually circular, die capillaries as molten threads or filaments into converging high-velocity heated gas (e.g., air) streams that attenuate the filaments of molten material to reduce their diameter, which may be to microfiber diameter. Thereafter, the meltblown fibers are carried by the high-velocity gas stream and are deposited on a collecting surface to form a web of randomly dispersed meltblown fibers. Such a process is disclosed for example, in U.S. Pat. No. 31,849,241 to Butin. Meltblown fibers are microfibers which may be continuous or discontinuous, are generally smaller than 10 microns in diameter, and are generally self bonding when deposited onto a collecting surface.

As used herein, the term "microfibers" means small-diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers may be found in, for example, U.S. Pat. No. 5,213,881, entitled "A Nonwoven Web With Improved Barrier Properties".

"Conventional hot-melt adhesive" means a formulation that generally comprises several components. These components typically include one or more polymers to provide cohesive strength (e.g., aliphatic polyolefins such as poly (ethylene-co-propylene) copolymer; ethylene vinyl acetate copolymers; styrene-butadiene or styrene-isoprene block copolymers, or other styrenic block copolymers or isoprene rubber materials; a resin or analogous material (sometimes called a tackifier) to provide adhesive strength (e.g., hydrocarbons distilled from petroleum distillates; rosins and/or rosin esters; terpenes derived, for example, from wood or citrus; etc.); perhaps waxes, plasticizers or other materials to modify viscosity (i.e., flowability) (examples of such materials include, but are not limited to, mineral oil, polybutene, paraffin oils, ester oils, and the like); and/or other additives including, but not limited to, antioxidants or other stabilizers.

A typical hot-melt adhesive formulation might contain from about 15 to about 35 weight percent polymer or polymers; from about 50 to about 65 weight percent resin or other tackifier or tackifiers; from more than zero to about 30 weight percent plasticizer or other viscosity modifier; and optionally less than about 1 weight percent stabilizer or other additive. It should be understood that other adhesive formulations comprising different weight percentages of these components are possible.

"Hot-melt processable" means that an adhesive composition may be liquefied using a hot-melt tank (i.e., a system in which the composition is heated so that it is substantially in liquid form; see, e.g., the adhesive-supply unit referred to in the Example 1 below) and transported via a pump (e.g., a gear pump or positive-displacement pump) from the tank to the point of application proximate to a substrate or other material; or to another tank, system, or unit operation (e.g., a separate system, which may include an additional pump or pumps, for delivering the adhesive to the point of application). Hot-melt tanks used to substantially liquefy a hot-melt adhesive typically operate in a range from about 100 degrees Fahrenheit to about 450 degrees Fahrenheit. Generally, at the point of application, the substantially liquefied adhesive composition will pass through a nozzle or bank of nozzles, but may pass through some other mechanical element such as a slot. A hot-melt processable adhesive composition is to be contrasted with a composition that requires an extruder, and the attendant pressures and temperatures characteristic of an extruder, to liquefy, mix, and/or convey the composition. While a hot-melt tank and pump in a hot-melt processing system can handle adhesive-composition viscosities in a range from about 100 centipoise to about 50,000 centipoise, an extruder can handle and process adhesive-composition viscosities in a range from about 10,000 centipoise to viscosities of several hundred thousand centipoise. An advantage of some adhesive compositions of the present invention is that said compositions are hot-melt processable. For example, adhesive compositions comprising blends of isotactic and atactic polymers, such as blends of isotactic and atactic polypropylene, generally may be substantially liquefied in a hot-melt tank and conveyed to the point of application via a pump.

Unless otherwise noted, "Laminated structure" or "laminate" means a structure in which one layer, material, component, web, or substrate is adhesively bonded—at least in part—to another layer, material, component, web, or substrate. As stated elsewhere in this application, a layer, material, component, web, or substrate may be folded over and adhesively bonded to itself to form a "laminated structure" or "laminate."

"Polymer", as used herein, generally includes, but is not limited to, homopolymers, copolymers, such as, for example, block, graft, random and alternating copolymers, terpolymers, and blends and modifications thereof.

"Softening Point" refers to the temperature at which a material softens or flows. It may be measured using ASTM E 28 (a determination of softening point using a ring-and-ball apparatus). It should be noted that the term "softening point" is generally used with regard to an amorphous material, amorphous polymer, or a predominantly amorphous material/polymer. If a material is crystalline, then the temperature at which the material softens and/or flows is the temperature at which the material changes sharply from a solid phase to a liquid phase. In this instance, the phase transition is characterized as the material's melting point, rather than its softening point. In the present application, a statement that a re-activatable adhesive's softening point is less than the softening point of a web, component, substrate, or strand means that the softening point of the re-activatable adhesive is less than the lower of either the softening point or the melting point of said web, component, substrate, or strand.

Representative Versions of Processes for Applying a Re-Activatable Adhesive to a Web, Component, Composite, and/or Strand In the process description that follows, the preparation, processing, and application of a re-activatable adhesive composition is described. It should be understood, however, that this description is given as an example. Other processing methods and equipment may be used to prepare and deliver various re-activatable adhesive compositions of the present invention to components used in the subsequent assembly of composites, disposable absorbent products and/or personal-care appliances for health, hygiene, or environmental applications.

Figure 1:
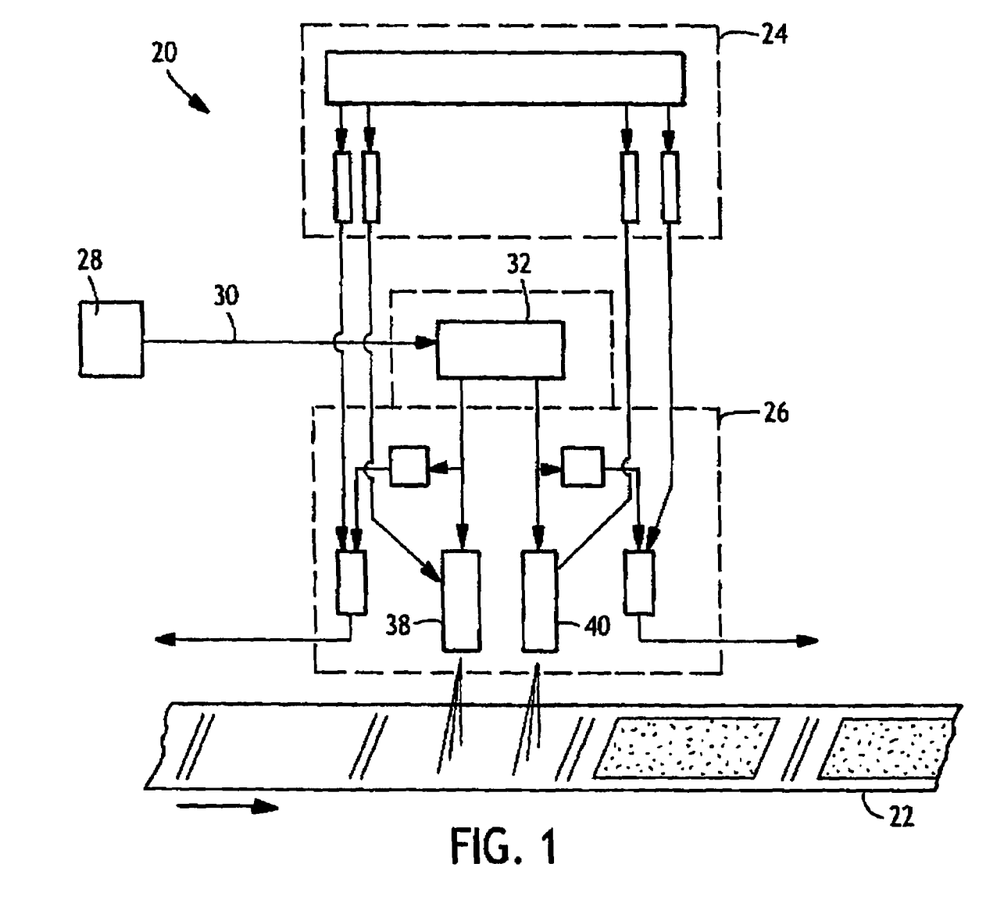
FIG. 1 depicts one representative version of a process for applying a re-activatable adhesive to component, in this case a web or substrate.

FIG. 1 shows a schematic diagram of an apparatus 20, and a method for spraying re-activatable adhesive composition, on a moving web 22. The apparatus 20 may include a programmable control system 24 that is operatively connected to a flow-control system 26. The combination of the programmable control system 24 and the flow-control system 26 are configured to control the delivery of a re-activatable adhesive composition in liquid form to the moving web 22. Generally a re-activatable adhesive composition will be received in solid form at a manufacturing site where equipment such as that depicted in FIG. 1 is located. For example, re-activatable adhesive compositions may be received as solid pellets, blocks, or some other shape. The solid is then heated so that the re-activatable adhesive composition is in a form such that it can be conveyed, and applied, to a substrate or other material. Usually this requires that the heated re-activatable adhesive be in substantially liquid form. For the present invention, a re-activatable adhesive composition, in solid form, might be received at a manufacturing site for heating and processing as described above. Alternatively, separate components of the re-activatable adhesive composition may be received and blended at the manufacturing site. An example of equipment and methods for heating an adhesive composition, or precursor materials to the adhesive composition, are described in more detail below.

The apparatus may also include a position-sensing system that is configured to sense a position of the moving web 22 and, in response thereto, generate a signal that is sent to the programmable control system 24.

As representatively illustrated in FIG. 1, the continuously moving web 22 may be supplied by any means known to those skilled in the art, such as known conveyor systems. The continuously moving web 22 can include any type of layer or web of material, such as: films; nonwoven webs; woven webs which may include strands of thermoplastic material; natural material such as threads of cotton and the like; laminate materials; or combinations thereof. As is described below in more specific terms, the re-activatable adhesive is sprayed on the continuously moving web 22 in a specific design or pattern for subsequent placement of or bonding to another material (i.e., after the re-activatable adhesive has been allowed to set; and after the input of energy—e.g., in the form of heat or ultrasonic energy—to "re-activate" the set adhesive). The other material can be the same or different than the web to which adhesive was applied. In some cases the re-activatable adhesive might be applied to both substrates, and the adhesive then allowed to set, before one or both adhesives are re-activated and the corresponding substrates joined together. Also, one substrate might be folded over and attached to itself to form a laminated structure after the adhesive has been re-activated. Or, as is discussed elsewhere, a substrate may be joined to an elastomeric material, such as an elastic strand. It should also be noted that the re-activatable adhesive may be applied such that the adhesive is uniformly coated in the surface of the web.

The programmable control system 24 of the present invention is configured to send signals to the flow control system 26 which, in response thereto, is configured to initiate a spray of re-activatable adhesive at the correct time to provide the desired pattern of adhesive on the moving web 22. Alternatively, the re-activatable adhesive can be applied in a continuous fashion, rather than in the form of discrete patterns. E.g., the adhesive might be applied using a slot coater, or in a meltblown pattern using nozzles, or in a swirl pattern, etc. As representatively illustrated in FIG. 1, the flow control system 26 includes an adhesive source 28 which is configured to deliver a re-activatable adhesive through an adhesive supply line 30 to a metering mechanism 32. The re-activatable adhesive can be delivered to the metering mechanism 32 by any means known to those skilled in the art, such as by the use of a pump.

The metering mechanism 32 is configured to continuously supply at least one independent, volumetric flow of re-activatable adhesive to a respective nozzle. As used herein, the term "volumetric flow" refers to a flow of re-activatable adhesive that has a predetermined volumetric flow rate. Such a "volumetric flow" may be provided by a positive-displacement metering pump which is configured to supply a specific volumetric flow which is independent of the manner in which the adhesive is supplied to the metering mechanism 32. As a result, for a re-activatable adhesive that is at a given density, the metering mechanism 32 is configured to provide an independent, predetermined mass flow rate of re-activatable adhesive to each nozzle. Other adhesive processing and delivery systems utilize pressure to provide a flow of adhesive. Note, as indicated elsewhere, that the re-activatable adhesive may be delivered using other devices, such as a slot coater, printing operation, or other such unit operation.

The metering mechanism 32 of the present invention may be configured to supply a single, volumetric flow of re-activatable adhesive to one nozzle or an independent, volumetric flow of re-activatable adhesive to each of a plurality of nozzles depending upon the number of nozzles required to provide the desired pattern (or substantially uniform application, or other) of re-activatable adhesive on the moving web 22. A suitable device to provide the metering mechanism 32 may include a positive-displacement metering pump which is commercially available from May Coating Technologies, Acumeter Division, a business having offices located in Holliston, Mass., under the trade designation No. 19539. The metering mechanism 32 may include any other piston pump or gear pump which are well known to those skilled in the art.

The metering mechanism 32 may be configured to supply any desired volumetric flow rate of re-activatable adhesive to each nozzle. For example, the metering mechanism 32 may be configured to provide a pre-determined volumetric flow rate of from about 1 to about 1000 cubic centimeters per minute and suitably from about 30 to about 180 cubic centimeters of re-activatable adhesive per minute to each nozzle. The metering mechanism 32 may be configured to provide either a constant or a variable volumetric flow rate of re-activatable adhesive to each nozzle. For example, if the metering mechanism 32 is a positive-displacement metering pump, the speed of the pump may be controlled to vary the volumetric flow rate of re-activatable adhesive to the nozzles.

Each nozzle 38 and 40 as representatively illustrated in FIG. 1 can be any device which is capable of providing the desired pattern (or other application, such as a substantially uniform application) of re-activatable adhesive on the moving web 22. For example, one suitable nozzle is commercially available from Nordson Corporation, a business having offices located in Duluth, Ga., under the trade designation Model No. 144906. Another suitable nozzle for use in the present invention is obtainable from ITW Dynatec Co. of Hendersonville, Tenn., under the trade designation number 057B1639, I.D. #A3. Such nozzles are typically configured to be operated between an on position and an off position to control the spray of re-activatable adhesive from the nozzles. When operated in the on position, each nozzle may be configured to spray substantially the entire volumetric flow of re-activatable adhesive which is independently supplied to it to more accurately control the amount and pattern of the re-activatable adhesive on the moving web. The nozzles 38 and 40 may further be configured to include air streams that can be directed to provide a desired pattern in the spray of re-activatable adhesive being dispensed from each nozzle. Such air streams can provide a desired re-activatable adhesive spray pattern, such as a pattern of swirls of said adhesive.

After the pattern, or other arrangement, of re-activatable adhesive has been sprayed on the moving web 22, the web may be further processed in a variety of ways. Generally the web will be provided with sufficient time for the applied re-activatable adhesive to set: i.e., to solidify. The time available for the adhesive to set may be reduced by "quenching" the adhesive (e.g., directing the web or substrate comprising the applied re-activatable adhesive to a roll that has been chilled or cooled so as to more rapidly reduce the temperature of the applied adhesive; by directing streams of cold air toward the web or substrate; etc.). After the re-activatable adhesive has set, the web can be directed to a winder so that the web comprising the re-activatable adhesive is wound up to form a roll of said web.

Figure 2:
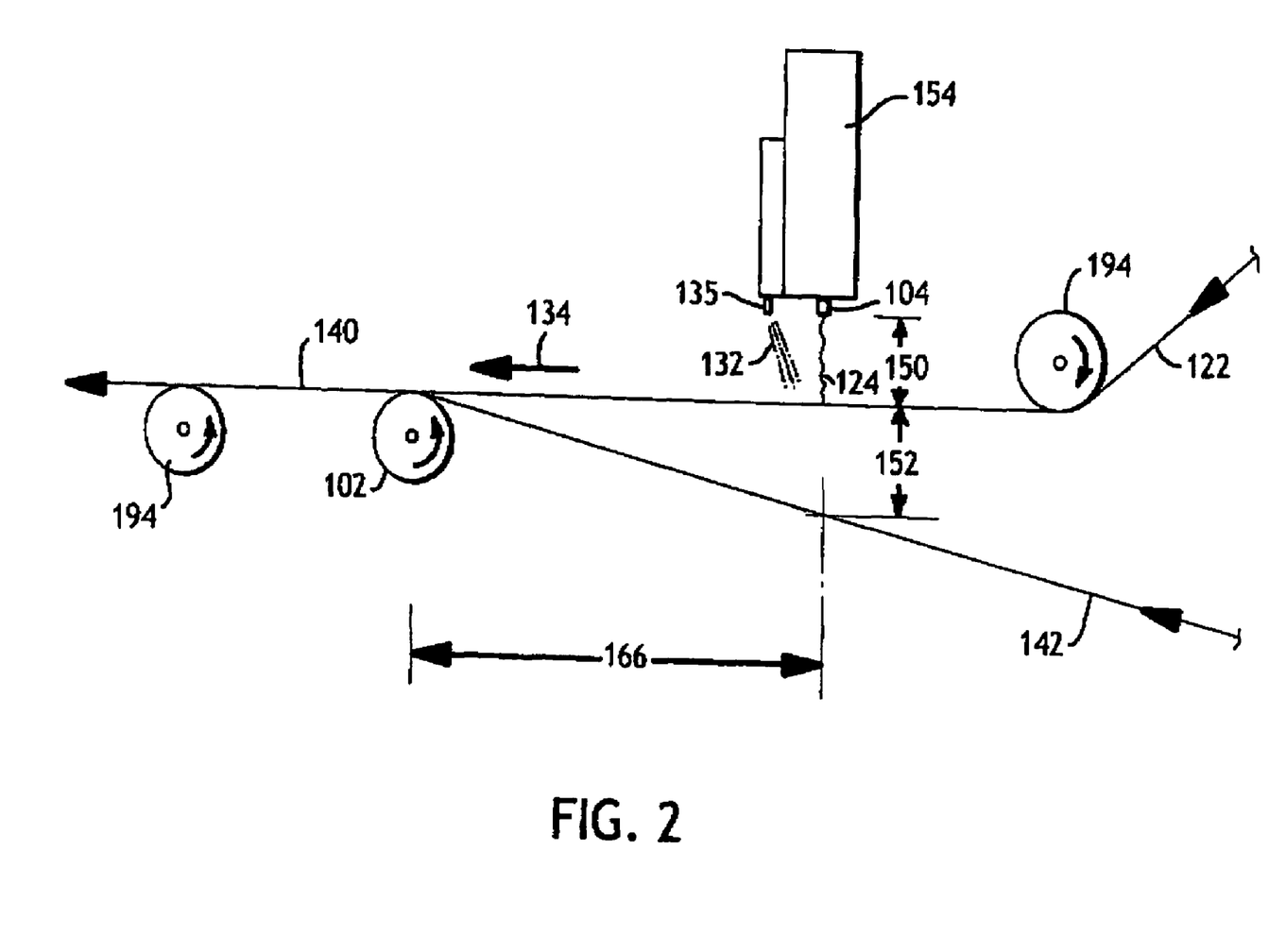
FIG. 2 depicts one representative version of a process for applying a re-activatable adhesive to a component, in this case an elastic strand.
Figure 4:
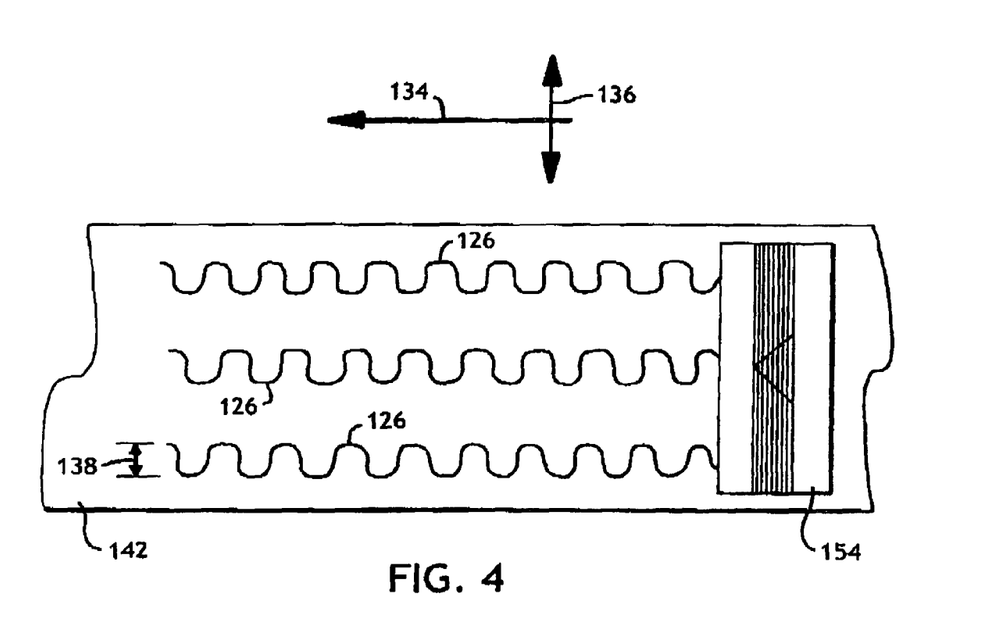
FIG. 4 depicts a representative version of a configuration of a re-activatable adhesive applied to a component, in this case a web or substrate.
Figure 4A:
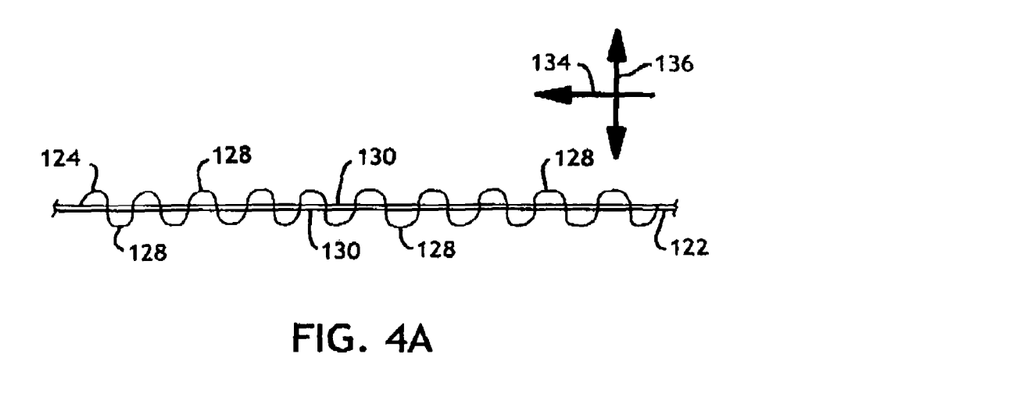
FIG. 4A depicts a representative version of a configuration of a re-activatable adhesive applied to a component, in this case an elastic strand.

Re-activatable adhesive may also be applied to other components of a disposable absorbent article or a personal-care appliance for health, hygiene, or environmental applications. For example, a reactivatable adhesive may be applied to an elastomeric component, such as a film or strand. With reference to FIGS. 2, 4 and 4A, a further aspect of the invention can include a moving of a strand of material, such as the shown material strand 122, at a selected speed along its appointed machine-direction 134. A substantially continuous filament 124, such as a filament of re-activatable adhesive, can be directed onto the strand of material (which, optionally, can be under tension) along an oscillating filament path 126, and the filament 124 can be arranged to provide a plurality of filament threads extending, or otherwise disposed, from opposed lateral side regions 130 of the strand of material 122. An air stream 132 can also be directed to operatively rope or otherwise wrap the filament threads around the strand of material 122. Desirably, a majority of the filament threads are wrapped around their corresponding strand of material. More desirably, substantially all of the filament threads are wrapped around their corresponding strand 122.

In particular aspects of the invention, the filament can be arranged to provide a plurality of overlaps between the filament 124 and its corresponding strand 122. The overlaps can, for example, extend generally cross-wise of the strand, and can be arranged in a selected series or other pattern along the longitudinal, machine-direction length of their corresponding strand. In other aspects of the invention, the air stream 132 can be directed to break or otherwise separate the filament 124 into thread segments that are attached in the cross-wise alignment onto their corresponding strand of material.

In still other aspects, the directing of the substantially continuous filament of re-activatable adhesive 124 onto the strand of material 122 can provide the filament threads in the form of a plurality of filament arches 128 which extend from or are otherwise disposed at the lateral side regions 130 of the strand of material 122. Desired arrangements of the adhesive filament can provide a plurality of substantially continuous filament arches, and the arches may be arranged in an alternating, staggered pattern with respect to their corresponding, individual strand of material. In further aspects, the technique of the invention can further include a contacting of the strand of material and wrapped re-activatable adhesive—after the adhesive has been allowed to set—onto a selected substrate, such as the base layer 142, to form a substrate composite 140. A source of energy, e.g. ultrasonics equipment, heat-transfer equipment such as a heated roll or heated embossed roll, high-speed rotary pressure-binding equipment, or other such unit operation (not shown) is used to activate the adhesive so that it can be used to adhere the strand to the substrate—as stated above, this may be done such that the adhesive is re-activated at discrete or intermittent locations to help optimize the balance of strength/integrity, softness/flexibility, and elasticity being sought. Alternatively, the strand of material and wrapped re-activatable adhesive are not immediately applied to a substrate, but instead are given sufficient time for the re-activatable adhesive to set before the strand is re-wound to form a spool, bobbin, or reel of the strand wrapped in the re-activatable adhesive. As mentioned above, a roll that is chilled or cooled, jets of cold air, or other unit operations may be used to accelerate the reduction of the adhesive's temperature so that it sets more quickly.

A suitable supply source, such as the representatively shown applicator 154, can direct an individual, substantially continuous filament 124 of the desired material onto each individual strand of material 122 along an individual oscillating filament path 126. In the representatively shown arrangement, the selected filament is composed of re-activatable adhesive. The position of the adhesive filament 124 is reciprocated in a substantially continuous, back-and-forth motion to provide the desired oscillating filament path 126 which crosses over the material strand 124 and extends past the cross-directionally opposed, lateral side regions 130 of the strand. The combination of the oscillating filament path and the machine-directional movement of the strand of material can cooperate to form a plurality of filament threads, such as the representatively shown filament arches 128, which are serially disposed at and extend from the laterally opposed side regions 130 of each individual strand of material. With respect to each individual strand of material, the positioning of the resulting series or sequence of filament arches alternates from one side of the material strand to the other side of the strand. Along the longitudinal machine-direction of the strand, the immediately adjacent arches are offset and staggered from each other by approximately one-half cycle of their corresponding, oscillating filament path 126.

The desired air stream 132 can be provided by any conventional air directing mechanism, such as a nozzle, tube, orifice, annulus, deflector, vane or the like, as well as combinations thereof. With reference to FIG. 2, the mechanism for delivering the air stream 132 may include a system of air jetting nozzles 135 which are separately constructed from the first applicator 154. Alternatively, the air jetting nozzles 135 may be configured as integrated portions or components of the first applicator 154 (e.g. FIGS. 3 through 3B). There may be one air-jet nozzle, or a plurality of air-jet nozzles as depicted in FIGS. 3 and 3B.

The applicator 154 may, for example, include a system of air jets which extrude or otherwise help to draw the desired adhesive filament 124 from the applicator. The system of air jets may also be employed to substantially simultaneously provide the desired air streams 132 for wrapping the desired portions of the re-activatable adhesive filaments 124 about their corresponding material strands 122. Accordingly, the directing of the air stream can be conducted in cooperation with the directing of the filament of re-activatable adhesive. In the various configurations of the invention, each air jet 135 (whether one or a plurality) and its corresponding air stream 132 can be oriented generally perpendicular to the local machine-direction 134. In particular arrangements of the invention, the air jet 135 and associated air stream 132 may be selectively tilted or otherwise angled along the machine-direction, and the amount of angle can be within the range of about ±45° relative to a line that is perpendicular to the local machine-direction, as representatively shown in FIG. 2.

Figure 3:
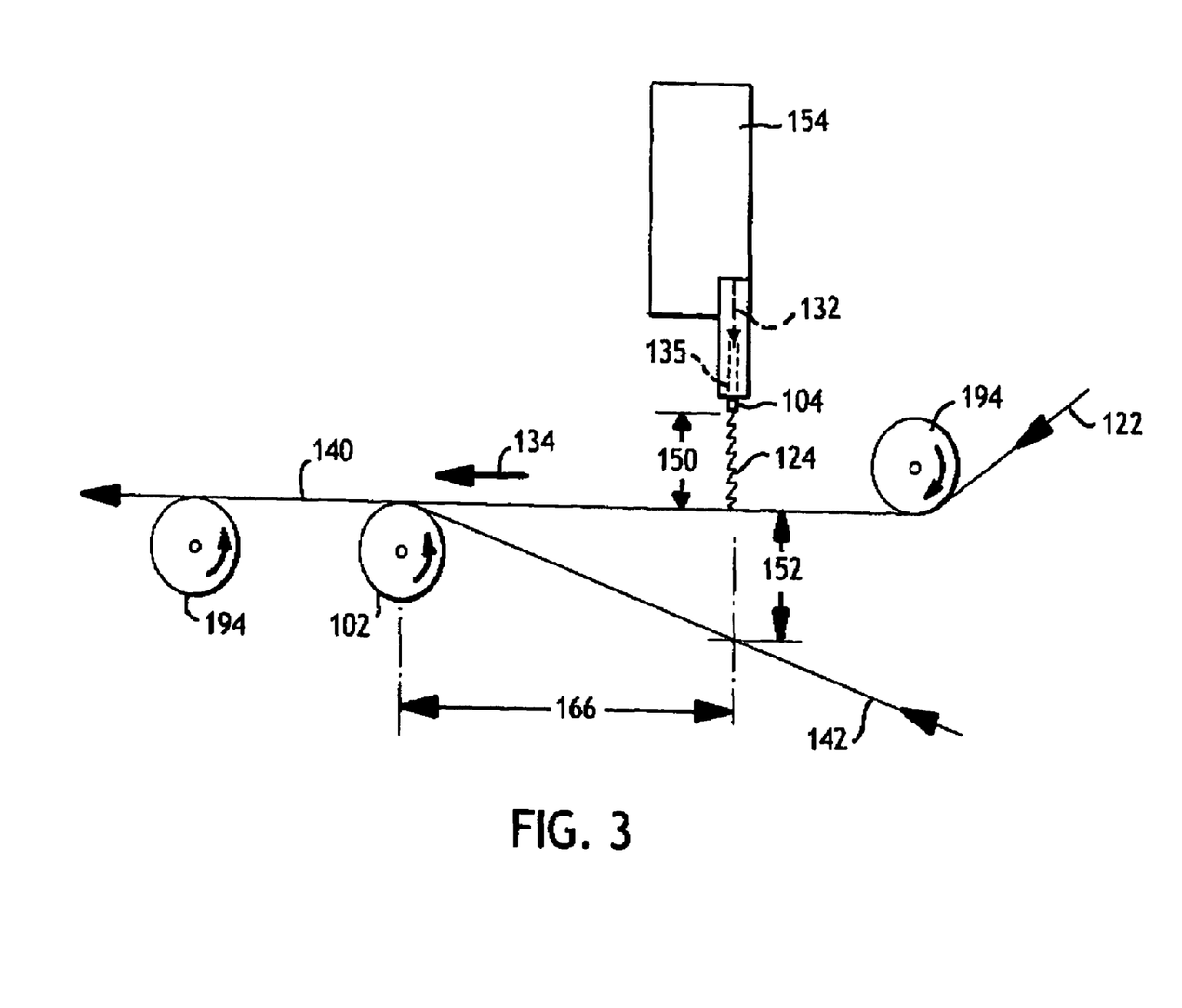
FIG. 3 depicts one representative version of a process for applying a re-activatable adhesive to a component, in this case an elastic strand.

With reference to FIGS. 2 and 3, particular aspects of the invention can provide a selected gap distance 150 between the applicator nozzles 104 and their corresponding material strands 122 (also strands 156, and/or 162). In particular aspects, the nozzle-strand gap distance 150 can be at least a minimum of about 4 mm. The nozzle-strand gap distance can alternatively be at least about 8 mm, and optionally, can be at least about 12 mm to provide improved performance. In other aspects, the nozzle-strand gap distance 150 can be not more than a maximum of about 28 mm. The nozzle-strand gap distance can alternatively be not more than about 24 mm, and optionally, can be not more than about 20 mm to provide improved effectiveness. For example, the nozzle-strand distance 150 can be important for regulating the size and distribution of the filament threads or arches 128 along the lateral side regions of each material strand.

In another aspect of the invention, the technique can provide a gap distance 152 between the material strands and their associated substrate layer (if any; as discussed above, in one embodiment of the invention, the elastomeric material treated with the re-activatable adhesive is directed to a re-wind stand for re-winding the elastomeric material after the re-activatable adhesive has set—with any optional acceleration of the setting time by using, for example, a cold roll), such as the base layer 142 and/or the laminate composite 148. In desired configurations, the gap distance 152 can be at least a minimum of about 3 mm. The gap distance can alternatively be at least about 4 mm, and optionally, can be at least about 5 mm to provide improved performance. In other aspects, the gap distance 152 can be not more than a maximum of about 12 mm. The gap distance can alternatively be not more than about 9 mm, and optionally, can be not more than about 7 mm to provide improved effectiveness. For example, the strand-substrate gap distance 152 should be large enough to obtain the desired wrapping of each individual adhesive filament 124 around its corresponding material strand.

Still other aspects of the invention can provide a selected machine-direction, separation distance 166 between the location of the applicator nozzles 104 and the location of their associated assembly mechanism (e.g. assembly roller), or, in some embodiments, a re-wind stand for re-winding the strand comprising the re-activatable adhesive. In particular aspects, the separation distance 166 can be at least a minimum of about 15 cm. The separation distance 166 can alternatively be at least about 20 cm, and optionally, can be at least about 25 cm to provide improved performance. In other aspects, the separation distance 166 can be not more than a maximum of about 200 cm. The separation distance 166 can alternatively be not more than about 125 cm, and optionally, can be not more than about 25 cm to provide improved effectiveness. For those embodiments where the elastomeric material comprising a re-activatable adhesive is not applied to a substrate, but is re-wound, then distance 166, coupled with the linear speed of the strand in the direction of travel 134, should allow for sufficient time for the re-activatable adhesive to set before the elastomeric material is rewound.

For those embodiments where the strand comprising the re-activatable adhesive is applied to a substrate 142, then the nozzle-assembly, separation distance 166 is desirably selected to allow re-activatable adhesive to set before contacting the substrate with the concurrent input of energy to re-activate the adhesive at a location proximate to the strand being joined to the substrate. In particular aspects, the time between the application of the re-activatable adhesive filament and the assembly of the material strand can provide an applicator-assembly time which is at least a minimum of about 0.003 sec. The applicator-assembly time can alternatively be at least about 0.004 sec, and optionally, can be at least about 0.005 sec to provide improved performance. Other times may be selected to provide time sufficient for the re-activatable adhesive to set. And, again, as noted elsewhere, a cold roll, directed flows of cold air, or other equipment may be used to accelerate the rate at which heat is conducted from the adhesive (i.e., the rate at which the temperature of the adhesive decreases) so that the adhesive sets more rapidly.

Figure 3A:
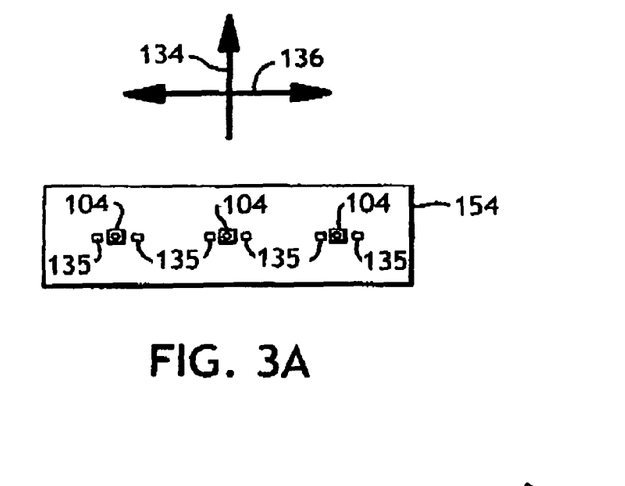
FIGS. 3A and 3B depict representative versions of equipment and/or processes for applying a re-activatable adhesive to a component, in this case an elastic strand.
Figure 3B:
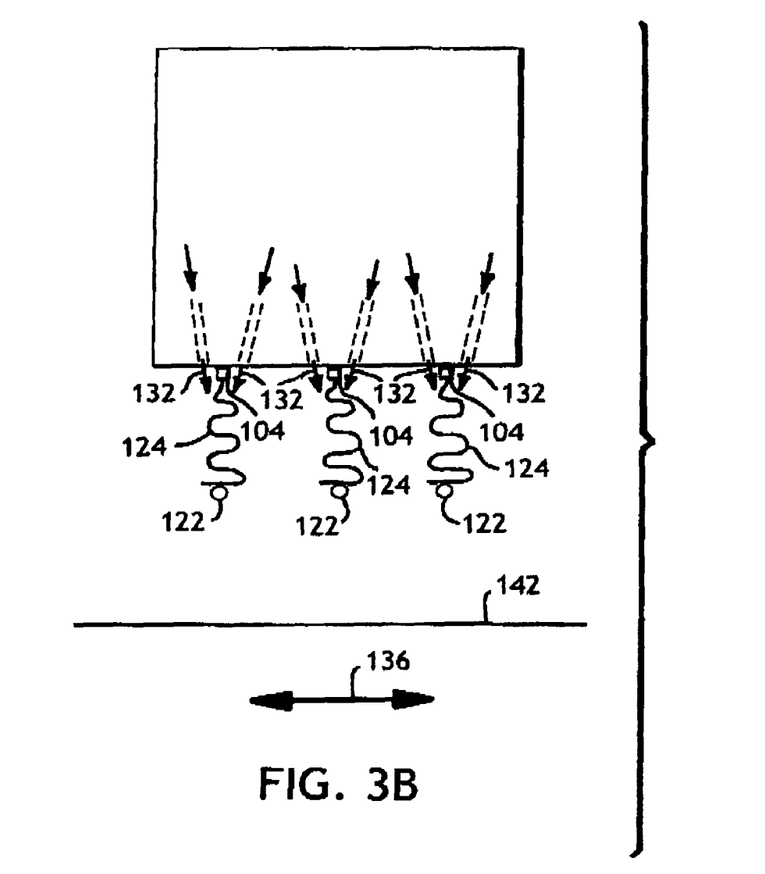

With reference to FIGS. 3 through 3B the applicator 154 may include a plurality of applicator nozzles 104, and each applicator nozzle can have an associated system of immediately adjacent air jets 135. The applicator nozzles 104 and the air jets 135 are aligned generally along the local cross-direction 136, and each applicator nozzle 104 has a cooperating pair of air jets 135. An air jet is located at each cross-directional, lateral side of its corresponding applicator nozzle, and each air jet is oriented generally perpendicular to the local machine-direction 134. In particular arrangements of the invention, the air jets 135 and their associated air streams 132 may be selectively tilted or otherwise angled along the cross-direction, and the amount of angle can be within the range of about ±15° relative to a line that is perpendicular to the local machine-direction (e.g. FIG. 3B). In desired arrangements, each air jet can be tilted by the selected angle to direct its air stream in a direction that is slanted toward its corresponding applicator nozzle.

In the various configurations of the invention, the desired temperature of the employed re-activatable adhesive can depend on the particular composition of the adhesive material. It has been found that a warmer temperature provides a relatively better distribution pattern of the re-activatable adhesive filaments 124. If the re-activatable adhesive temperature, however, is too high, the adhesive can excessively degrade and the re-activatable adhesive filament 124 may exhibit excessive breakage.

In particular aspects, the material of the filament 124 can be provided at a viscosity which is at least a minimum of about 1,000 centipoise (cP) (at a temperature of 160 degrees Celsius). The viscosity can alternatively be at least about 12,000 cP, and optionally, can be at least about 16,000 cP to provide improved performance. In other aspects, the viscosity can be not more than a maximum of about 50,000 cP. The viscosity can alternatively be not more than about 22,000 cP, and optionally, can be not more than about 19,000 cP to provide improved effectiveness. It should be noted that for some materials, for example materials comprising ethyl vinyl acetate, the viscosity of the material at 350 degrees Fahrenheit may reach 100,000 cP; suitably 250,000 cP; or even higher.

In additional aspects, the filament 124 can be provided at a filament speed which is at least a minimum of about 0.04 m/sec. The filament's speed can alternatively be at least about 0.06 m/sec, and optionally, can be at least about 0.3 m/sec to provide improved performance. In other aspects, the filaments speed can be not more than a maximum of about 5 m/sec; suitably not more than a maximum of about 10 m/sec; particularly not more than a maximum of about 15 m/sec. The filaments speed can alternatively be not more than about 3 m/sec, and optionally, can be not more than about 1.4 m/sec to provide improved effectiveness.

The air pressure delivered to the one or more re-activatable adhesive applicators can be provided at a selected pressure. In particular aspects, the directing of the air stream 132 can include an expelling of the air stream under an air pressure which can be at least a minimum of about 7 KPa (gauge). The air pressure can alternatively be at least about 20 KPa, and optionally, can be at least about 27 KPa to provide improved performance. In other aspects, the air pressure can be not more than a maximum of about 140 KPa. The air pressure can alternatively be not more than about 103 KPa, and optionally, can be not more than about 55 KPa to provide improved effectiveness.

If the pressure is too low, the adhesive filaments 124 may not be distributed in the desired oscillating pattern, and there may be insufficient wrapping of the re-activatable adhesive filaments about their corresponding material strands. A relatively higher pressure can provide a larger distribution pattern over a greater cross-directional distance. The greater air pressure, however, can produce a finer, relatively smaller diameter adhesive filament 124, but the higher air pressure may generate excessive "blow-by" of the re-activatable adhesive in a separation away from the corresponding material strands.

In particular aspects, the directing of the air stream 132 can provide an air stream speed which is at least a minimum of about 38 m/sec. The air stream speed can alternatively be at least about 190 m/sec, and optionally, can be at least about 380 m/sec to provided improved performance. In other aspects, the air stream speed can be not more than a maximum of about 3800 m/sec. The air stream speed can alternatively be not more than about 1900 m/sec, and optionally, can be not more than about 800 m/sec to provide improved benefits.

The directing of the filament of adhesive 124 along the oscillating filament path 126 can extend over an overall, cross-directional traversing distance 138 (e.g. FIG. 4) which can be at least a minimum of about 0.01 cm. The traversing distance can alternatively be at least about 0.1 cm, and optionally, can be at least about 0.2 cm to provide improved performance. In other aspects, the traversing distance can be not more than a maximum of about 0.6 cm. The traversing distance can alternatively be not more than about 0.5 cm, and optionally, can be not more than about 0.4 cm to provide improved effectiveness. In desired configurations, the oscillating filament path 126 can operatively traverse the filament 124 past both laterally opposed side regions 130 of the selected material strand by substantially equal distances.

In still other aspects, the filament path 126 can be configured to reciprocate back-and-forth at a traversing frequency which can be at least a minimum of about 100 Hz (Hertz). The frequency can alternatively be at least about 500 Hz, and optionally, can be at least about 1,000 Hz to provided improved performance. In other aspects, the frequency can be not more than a maximum of about 10,000 Hz. The frequency can alternatively be not more than about 6,000 Hz, and optionally, can be not more than about 4,500 Hz to provide improved effectiveness. In a desired configuration, the frequency can be about 1200 Hz.

The directing and depositing of the filament of re-activatable adhesive 124 onto the selected strand of material can provide an adhesive add-on which can be at least a minimum of about 0.004 grams of re-activatable adhesive per meter of length of the corresponding strand material (g/m). The re-activatable adhesive add-on can alternatively be at least about 0.008 g/m, and optionally, can be at least about 0.012 g/m to provided improved performance. In other aspects, the re-activatable adhesive add-on can be not more than a maximum of about 0.24 g/m. The re-activatable adhesive add-on can alternatively be not more than about 0.07 g/m, and optionally, can be not more than about 0.04 g/m to provide improved effectiveness.

The air stream 132 can be directed to operatively wrap a substantial majority of the filament arches 128 around their corresponding strand of material 122. In particular aspects, the directing of the air stream 132 can operatively deposit and maintain at least about 60% of the filament threads or arches 128 onto their corresponding material strands (e.g. strands 122, 156 and/or 162). Alternatively, the directing of the air stream 132 can operatively deposit at least about 75% of the filament threads onto their selected strands of material, and optionally can operatively deposit at least about 90% of the filament threads onto their selected strands of material. In desired configurations, the directing of the air stream can operatively deposit substantially 100% of the filament threads onto their selected material strands.

In other aspects, the directing of the air stream 132 can be configured to detach not more than about 40 wt % of the directed re-activatable adhesive away from the corresponding strands of material. The directing of the air stream can alternatively detach not more than about 25 wt % of the directed re-activatable adhesive away from the strand of material, and optionally, can detach not more than about 10 wt % of the directed re-activatable adhesive away from the corresponding strands of material.

In further aspects, the moving of the selected strand of material can provide a strand speed which is at least a minimum of about 0.05 m/sec. The strand speed can alternatively be at least about 0.25 m/sec, and optionally, can be at least about 3 m/sec to provide improved performance. In other aspects, the strand speed can be not more than a maximum of about 10 m/sec. The strand speed can alternatively be not more than about 6 m/sec, and optionally, can be not more than about 5 m/sec to provide improved effectiveness.

While various aspects or features of the invention have been described with respect to the particular applicator 154, it should be readily apparent that such features may be incorporated at various other locations within the technique of the invention. For example, the features may be additionally or alternatively incorporated at the locations of applicators 158 and/or 164. Suitable applicator devices can include an ITW Model, OMEGA UFD device, as previously described in detail.

Of course, as stated above, the re-activatable adhesive may be applied in other ways. For example, the adhesive may be applied to a component using an extruder, a slot coater, or other equipment for conducting and delivering heated material to a component such as a substrate or strand. Alternatively, the re-activatable adhesive may be meltblown onto a substrate or web.

It should also be noted that the above examples are just a few of the versions of the present invention by which a re-activatable adhesive may be applied to a web, component, composite, and/or strand. Other processes may be used, so long as the result is a web, component, composite, or strand which has been treated with a re-activatable adhesive and allowed sufficient time for at least some portion of the re-activatable adhesive to set. Thereafter, by inputting energy to activate the adhesive, the web, component, composite, or strand may be joined or bonded to some other web, component, composite, or strand. Prior to the re-activatable adhesive being activated, the web, component, composite, or strand may be conveniently handled without having to accommodate the tackiness normally attendant to liquefied hot-melt adhesives. Furthermore, if the web, component, composite, or strand comprising the re-activatable adhesive is unwound at a process different or separate from that at which the web, component, composite, or strand was prepared, then the web, component, composite, or strand comprising the re-activatable adhesive may be conveniently joined to other materials without the problems or issues attendant to liquefying and applying a hot-melt adhesive at the same process location.

The re-activatable adhesive can be applied by an extruder, drum unloader, grid melter, in the form of meltblown/spray/slot coating on a web, such as an elastic film. The coated elastic film is wound up, transferred to product converting line, and then unwound, slip-cut into patches and placed on product web. The coated elastic film is then reactivated via thermal, pressure, ultrasonic, or other means and bonded into the product.

The reactivatable adhesive may be applied by meltblown (MB) spraying, slot coating, printing, beading, strands, swirl, gravure, or streaking onto one or both surfaces of a web, including a film or laminate. The method of winding, transfer, and reactivation in converting as previously described could be used to incorporate the elastic member into product.

Representative Versions of Processes for Making Higher-Order Assemblies Comprising a Web, Component, Composite, and/or Strand Comprising a Re-Activatable Adhesive In the description that follows, representative versions of processes for making higher-order assemblies (e.g., a product, or a sub-assembly in a product) comprising a web, component, composite, and/or strand comprising a re-activatable adhesive are described. It should be understood, however, that this description is given as an example. Other processing methods and equipment may be used to prepare such assemblies, including, for example disposable absorbent products and/or personal-care appliances for health, hygiene, or environmental applications.

Once a web, component, composite, or strand comprising a re-activatable adhesive has been prepared, it may be used in a variety of ways such as in the construction of disposable absorbent articles. Alternatively, the web, component, composite, or strand may be used for various personal-care appliances for health, hygiene, and/or environmental applications. Examples of such articles and appliances include, but are not limited to, diapers, baby wipes, training pants, swim pants, and other related disposable garments and products; feminine-care products, including sanitary napkins, wipes, menstrual pads, panty liners, panty shields, catamenial articles, interlabial inserts, tampons, tampon applicators, menstrual garments, and other related disposable garments and products; adult-care products, including wipes, pads, containers, incontinency products, incontinency garments, urinary shields, and other related disposable garments and products; service, industrial, and household products, including wipes, towels, bath tissue, paper towels, hand towels, napkins, facial tissue, and other related disposable garments and products; nonwoven materials, including nonwoven roll goods and other related disposable products; home-comfort products, including pillows, pads, cushions, masks, and other related disposable products; body care products, including products for cleansing or treating the skin and other related disposable products, such as spa-related products; professional and consumer health-care products, including products for applying hot or cold therapy, wraps or supports for joints or other body parts, surgical drapes, upper-respiratory-health products, infection-control products, temperature-management products, face masks, hospital gowns, wipes, wraps, covers, containers, filters, and other related disposable garments and products; household cleaning products; and the like.

The web, component, composite, or strand may be used in any health-and-hygiene product, such as a disposable absorbent article. The primary difference between use of the present invention, and past practice, is that the present invention is directed to a web, component, composite, or strand in which the re-activatable adhesive has been allowed to set, thus facilitating handling of the web, component, composite, or strand before the adhesive is activated. Furthermore, the present invention allows for selectivity in activating those portions or locations of the adhesive desired for the article of manufacture. As noted above, generally, at a location where two components are joined by an adhesive, that location—which comprises the attached combination of the two components and the adhesive—is thicker and stiffer than those locations where the two components remain unattached. The greater the number of such attachment locations, the greater the likelihood that the resulting composite comprising these two glued-together components is stiff. By using processes for selectively inputting energy such as thermal point bonding or ultrasonics unit operations, the re-activatable adhesive can be activated at only those locations desired by the manufacturer.

If preparation of the component comprising a re-activatable adhesive is decoupled from the process by which a composite or product is made with said component, other benefits may be realized. First, if desired, the speed at which the component comprising a re-activatable adhesive is prepared may be different than the speed at which the composite or product employing said component is made. So, for example, the speed at which the component is prepared may be run slower to achieve a more uniform coating of the re-activatable adhesive or for some other desired benefit. A slower speed also allows for an increased time for the re-activatable adhesive to set prior to the component being wound up or accumulated in some other way prior to use when making a higher-order assembly comprising the component (e.g., a product). Second, by decoupling these processes, a manufacturing operation by which a product employing a component comprising a re-activatable adhesive is made may be more efficient, cleaner, and simpler. Also, decoupling the processes facilitates one company making and selling the component comprising a re-activatable adhesive, and another company purchasing and employing said component in a product.

Another benefit generally, in some cases, is the possible reinforcement of the component to which the re-activatable adhesive is applied. So, for example, applying a re-activatable adhesive comprising a blend of atactic and isotactic polypropylene materials can serve to reinforce the substrate to which it is applied, such as a nonwoven material comprising polypropylene fiber. As noted above, the re-activatable adhesive can be formulated so that its softening point is lower than the softening point of the material to which the adhesive is applied. In this example, the blend of atactic and isotactic polypropylene polymers may be selected so that the blend has a softening point that is lower than that of the polypropylene fiber used in making the substrate. In this way the adhesive, when applied at or above its softening temperature, is less likely to degrade the substrate. Furthermore, when the adhesive is re-activated, the inputted energy may be selected so that the adhesive becomes tacky (i.e., begins to liquefy), but the substrate maintains its integrity (i.e., it substantially maintains its solid form). Blends of amorphous and crystalline polymers for binding are discussed in U.S. Patent Application No. 60/259,037, entitled "Hot-Melt Adhesive Based on Blend of Amorphous and Crystalline Polymers for Multilayer Bonding," filed on 29 Dec. 2000. This application is incorporated by reference in its entirety in a manner consistent herewith.

Webs, components, composites, and strands comprising a re-activatable adhesive may be incorporated into a number of composites or products. Examples of such composites and/or disposable absorbent articles are described in U.S. Pat. No. 4,940,464, entitled "Disposable Incontinence Garment or Training Pant," which is hereby incorporated by reference in its entirety; U.S. Pat. No. 5,904,675, entitled "Absorbent Article with Improved Elastic Margins and Containment System," which is hereby incorporated by reference in its entirety, with column 7, lines 7 through 34 discussing use of elastic strands with a containment flap, and column 9, line 29 through column 10, line 36 discussing elastic members; U.S. Pat. No. 5,904,672, entitled "Absorbent Article having Improved Waist Region Dryness and Method of Manufacture," which is hereby incorporated by reference in its entirety, with column 11, line 39 through column 12, line 2 discussing elastic leg members; and U.S. Pat. No. 5,902,297, entitled "Absorbent Article Having a Collection Conduit," which is hereby incorporated by reference in its entirety. It should be understood that the present invention is applicable to other structures, composites, or products incorporating one or more elastic strands.

As stated above, the web, component, composite, or strand comprising the re-activatable adhesive will be exposed to thermal, infrared, ultrasonic, or other forms of energy in subsequent unit operations or processing steps. For example, at a location proximate to the location at which a strand comprising a re-activatable adhesive is joined to a substrate, the strand, or the combination of the stand and substrate, may pass through an ultrasonic-bonding unit operation wherein the strand, the substrate, or both are exposed to ultrasonic energy. Referring to PCT International Publication Number WO 99/25296, which is hereby incorporated by reference in its entirety in a manner consistent with the present document, the publication discloses the use of ultrasonic bonding to form side seams or seals in the disposable underpant. (See, e.g., page 29, lines 10-25; additional detail regarding the forming of such side seals is disclosed in U.S. Pat. No. 4,610,681, which issued on 9 Sep. 1986 and is entitled "Disposable Underpants Having Discrete Outer Seals," and which is hereby incorporated by reference in a manner consistent herewith; and U.S. Pat. No. 4,641,381, which issued on 10 Feb. 1997 and is entitled "Disposable Underpants, Such as Infant's Training Pants and the Like," which is also incorporated by reference in a manner consistent with the present document.).

Specific examples composite materials, laminates, and disposable absorbent articles with which re-activatable adhesives of the present invention may be utilized are disclosed in the following U.S. patents and U.S. patent applications: U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al; U.S. Pat. No. 5,192,606 issued Mar. 9, 1993, to Proxmire et al.; U.S. Pat. No. 5,904,675, entitled "Absorbent Article with Improved Elastic Margins and Containment System." Each of the preceding U.S. patents is incorporated by reference in its entirety and in a manner consistent with the present document. It should be understood that the present invention is applicable to other structures, composites, or products incorporating re-activatable adhesive compositions of the present invention.

Representative Versions of Re-Activatable Adhesive Compositions

Re-activatable adhesives may be prepared using a variety of chemistries. The chemistry may be selected based on its ability to adhere to, and function as an adhesive with, the webs, components, composites, or strands that are anticipated to be joined to one another. One criterion for selection is the softening point of the selected chemistry of the re-activatable adhesive compared to the softening point(s) of the webs, components, composites, or strand to be treated with said adhesive. Frequently the chemistry will be selected so that the re-activatable adhesive has a lower softening point compared to the softening point(s) of the materials to be treated with the adhesive. By selecting the chemistry of the re-activatable adhesive so that it does have a lower softening point compared to the softening point of the materials to be treated with the adhesive (as well as other materials which will be joined to the web, composite, component, or strand comprising the re-activatable adhesive), the amount of energy needed to activate the adhesive is lessened. Furthermore, the integrity of the web, composite, component, or strand to which the adhesive is associated (as well as the integrity of the other materials which will be joined to the web, composite, component, or strand comprising the re-activatable adhesive) is maintained, in that the inputted energy is sufficient to activate (i.e., make tacky) the re-activatable adhesive, but is not sufficiently high to soften and/or melt the other materials that are being joined. In some versions of the invention, the chemistry of the re-activatable adhesive is selected to have a softening point between about 60 degrees Celsius and about 160 degrees Celsius. Suitably the softening point or temperature is between about 60 degrees Celsius and about 150 degrees Celsius. The softening point or temperature may also be between about 60 degrees Celsius and about 140 degrees Celsius. Alternatively, the softening point of the re-activatable adhesive may be between about 60 degrees Celsius and about 130 degrees Celsius. Or the softening point of the re-activatable adhesive may be between about 60 degrees Celsius and about 100 degrees Celsius Possible polymers to use in re-activatable adhesive compositions include, for example, ethylene-vinyl acetate (EVA) copolymers, ethylene methyl acrylate (EMA), amorphous poly-alpha olefins (APAO), isotactic polypropylene (i-PP), atactic polypropylene, high melt flow rate thermoplastic elastomers, such as SIS (styrene-isoprene-styrene), SBS (styrene-butadiene-styrene), SEBS (styrene-ethylene-butene-styrene), SEPS (styrene-ethylene-propylene-styrene), metallocene polyethylene copolymerized with octene and/or butene and/or hexane, as well other additives (tackifiers, plasticizer and antioxidant) commonly incorporated into adhesives, and the like, including combinations of the preceding.

One version of a re-activatable adhesive comprises atactic-polypropylene or poly-alpha-olefin (APAO) (e.g., 0-80% by weight of, for example, Eastman P1010 or P1023, both of which are amorphous polypropylene, available from Eastman Chemical Company, a business having offices at Kingsport, Tenn.; Rextac 2115, another amorphous or atactic polypropylene, available from Huntsman Polymer Co., a business having offices in Houston, Tex.; high melt flow crystalline polypropylene (e.g., 5-30% by weight of, for example, Sunoco CP15000P [melt flow rate of 500 to 2000] available from Sunoco Corporation, a business having offices at Pittsburgh, Pa., or Exxon PP 3746G, available from ExxonMobile Chemical Company, a business having offices at Houston, Tex.; high melt flow SEPS and/or SIS, metallocene polyethylene/polypropylene thermoplastic elastomers, and/or ethylene-vinyl acetate up to 30% by wt. (e.g. Septon polymers, available from Kurary Limited, Japan; Kraton polymers, available from Kraton Polymers, Inc., Houston, Tex.; Exxon Dexco SIS polymers available from ExxonMobile Chemical Company, Houston, Tex.; ESCORENE ULTRA, also available from ExxonMobile; Dupont Dow—Engage 8400 series, ELVAX 240, available from E. I. DuPont de Nemours & Company, Wilmington, Del.), as well tackifiers (20-65% wt, e.g., Escorez series from ExxonMobile, H-100 from Eastman Chemical) or other hydrocarbon resins from petroleum distillates, rosin and/or rosin esters, polyterpenes derived from wood or synthetic chemicals. Other additives (0~10% by weight) such as antioxidant (Irganox 1010 from Ciba specialty), colorant/filler (e.g. TiO2 or CaCO3), and viscosity modifiers (0~20%) such as mineral oil, can be used in the adhesive formulation.

EXAMPLES

Example 1

A 0.65 ounce-per-square-yard SMS (spunbond-meltblown-spunbond) material, available from Kimberly-Clark Corporation, was precoated by spraying a re-activatable adhesive, in this case a polypropylene-based adhesive material, at add-on levels of 5, 6, and 7.5 grams of adhesive per square meter of material (for each of two spray nozzles; see description below). The SMS material was a polypropylene meltblown layer sandwiched between two polypropylene spunbond layers, and had a melting point of about 170 degrees Celsius. The re-activatable polypropylene adhesive material, designated as SA-15s, was formulated by combining the following materials in the recited proportions (listed in percents by weight): 30% P1010 (an atactic polypropylene available from Eastman Chemical), 17% 3746G (a crystalline polypropylene available from ExxonMobil), 45% Escorez 5380 (a hydrocarbon tackifier available from ExxonMobil), 7.5% Septon 2002 (SEPS material, known as Septon polymer, available from Kurary Limited, Japan) and 0.5% Irganox 1010 (an antioxidant material available from Ciba Specialty Chemical). The re-activatable polypropylene adhesive had a softening point of about 312 degrees Fahrenheit, determined using ASTM E 28.

The web of SMS material was unwound at a speed of about 100 feet per minute. The web had a width of 126 mm. The web of material was directed to conventional equipment for melting and spraying a hot-melt adhesive on a web. The SA-15s polypropylene formulation, which, as stated above, had a softening point of about 312 degrees Fahrenheit determined using ASTM E 28 (a determination of softening point using a ring-and-ball apparatus), was heated and sprayed onto the web at each of the identified add-on levels (i.e., at 5, 6, and 7.5 grams per square meter) for each of two nozzles. The heated re-activatable adhesive was sprayed through two nozzles, the tips of which were approximately 3.5 inches from the surface of the web. The two nozzles were arranged such that two, 1-inch-wide strips of a random, meltblown-like pattern of adhesive was sprayed onto the surface of the web at the web's edge (leaving a 75-mm, uncoated swath in the middle of the web between the two, one-inch wide bands of re-activatable adhesive, with each of the bands at the edge of the web). The web was then directed to, and contacted, a chill roll, to accelerate cooling—and therefore setting—of the reactivatable adhesive. The surface of the web bearing the adhesive contacted the surface of the chill roll. The pre-coated web was then wound up in roll form, with the time between applying the re-activatable adhesive and wind-up of the roll being about 1-2 seconds or so.

A laboratory-scale ultrasonic bonder, the Branson 931 intelligent Actuator, available from Branson Ultrasonics Corporation, Danbury, Conn., was then used to sandwich elastic strands between two layers of the pre-coated SMS material (with the pre-coated, re-activatable adhesive oriented inward toward the elastic strands). The equipment was operated at a pressure of 350 kiloPascals and with a dwell time of about 0.05 to 0.1 seconds ("dwell time" refers to the time of contact between the horn and anvil of the laboratory scale ultrasonic bonder). A Lycra XA (T151) strand (with a linear density of 1100 DeciTex), available from Invista, having offices in Wichita, Kans., was stretched at 250% and sandwiched—while in a stretched condition—between two 0.65 ounce-per-square-yard pre-coated SMS layers, with the pre-coated re-activatable adhesive oriented inward toward the Lycra strand. The pattern on the anvil consisted of dots protruding from the surface of the anvil, with each dot having approximately a 1 mm diameter. The dots were uniformly located across the surface of the anvil, with the distance between dots in a given row being about 5 mm. The distance between individual rows of dots was about 2.5 mm. The percent bond area—i.e., that percent area of the anvil equating to the total area of the raised dots protruding from the surface of the anvil—was about 6%. Furthermore, the density of the raised dots was about 8 per square centimeter.

It should be noted that if ultrasonics equipment is used to input energy to reactivate the re-activatable adhesive, numerous other patterns may be selected, both for decorative and functional reasons. As note above, an advantage of the present invention is the ability to effect discrete bonding locations and bonding patterns. Accordingly, when ultrasonics equipment is used, different raised shapes, lines, or other configurations may be used to re-activate the re-activatable adhesive. Furthermore, the density and/or % bond area of these raised shapes, lines, or other configurations may be changed, depending on the properties sought for the composite employing the re-activatable adhesive (e.g., balancing stretchability, softness, and integrity of the composite).

We qualitatively tested the resulting composites by repeatedly stretching them to their maximum stretch. These representative composites of the invention remained intact during the repeated stretching—i.e., each had integrity and was adapted for use as an elastomeric material to be employed in higher-order assemblies. Composites made using the lowest add-on level (5 grams per square meter of re-activatable adhesive) and lowest dwell time (0.05 sec) looked and functioned well.

We compared the composites of the invention with a composite prepared in the same way using the laboratory-scale ultrasonics equipment, but without the SMS material being pre-coated with a re-activatable adhesive. Under the same ultrasonics operating conditions, we were unable to bond the Lycra strand to the SMS material. When attempting to bond the Lycra material to the SMS material without a re-activatable adhesive under more vigorous ultrasonic operating conditions, e.g. longer dwell times exceeding 0.1 seconds, the Lycra strand failed (i.e., sufficient energy was inputted into the strand that its polymeric constituents began to flow, thus facilitating separation of the strand).

Example 2

A 0.65 ounce-per-square-yard SMS (spunbond-meltblown-spunbond) material, available from Kimberly-Clark Corporation, was precoated in the same way, at the same add-on levels, and using the same re-activatable adhesive described in Example 1. But instead of making a representative composite of the present invention using laboratory-scale ultrasonics equipment, a roll of the pre-coated SMS material was slit in half along its length, so that two webs of pre-coated SMS material, each with a single band of adhesive, was formed. These two webs of the pre-coated SMS material were placed on unwind stands, with the webs being unwound and directed, at a line speed of about 390 feet per minute, to ultrasonics bonding equipment. Each of the two webs were folded to form a flattened "J" shape: i.e., a flat, linear portion of the "J" shape contiguous with a "U-shaped" lower portion, with each corresponding band of re-activatable adhesive being folded such that adhesive was located on opposing, inwardly-directed surfaces of the "U-shaped" lower portion of the "J." In this way, adhesive on one portion of an inwardly-directed surface would contact a strand and adhesive on another portion of the same inwardly-directed, but opposing surface of the U-shaped lower portion of the "J-shaped" web. Prior to the webs, and the opposing surfaces of re-activatable adhesive located on the interior surface of the U-shaped lower portion of the "J-shaped" web contacting one another between the horn and anvil of the ultrasonics equipment, two strands of Lycra XA (T151) from Invista (with a linear density of 1100 DeciTex) were unwound, stretched to an elongated length that was 250% greater than the length of the strand in its original spooled/wound form, and positioned as described above, with one strand enveloped within each U-shaped lower portion of the "J-shaped" web. I.e., the strand was positioned so that it would be sandwiched between re-activatable adhesive located on the interior, opposing surfaces of the U-shaped lower portion of the "J-shaped" web. Both webs, and the corresponding strands, were fed into the ultrasonics equipment so that the re-activatable adhesive on the inner, opposing surfaces of the U-shaped lower portion of the "J-shaped" web became tacky, thereby bonding and sandwiching the strand between the re-activatable adhesive layers to form a flattened, bonded, U-shaped lower portion of the "J-shaped" web (i.e., an elastomeric composite in which the elastic strand was bonded at discrete locations along its length to the SMS material).

The ultrasonics equipment included a DuKane model 3005 Auto Trace, 240 volt, ultrasonics unit operation with a 20 kilohertz generator and a 2-inch horn. As with the bench-scale ultrasonics equipment discussed in Example 1, an anvil with a raised dot pattern was used to re-activate the re-activatable adhesive. The equipment was operated at an anvil load pressure of 32 pounds per square inch and a dwell time of about 0.05 to 1 milliseconds. After the resulting composite exited the ultrasonics unit operation, it was incorporated into a conventional personal-care disposable absorbent article, in this case a diaper, by adhesively bonding the composite along its non-elasticized edge to the remaining portion of other components of the diaper. The composite was attached while in its fully elongated state, and then allowed to retract once bonded to the other diaper components. As stated above, a diaper is one version of a health-and-hygiene appliance that can employ various embodiments of the present invention.

The rotary ultrasonic bond had a pattern consisting of nine angled bands of bond-point regions, equally spaced (1.075 mm apart) along the axis of the strand location, and end capped by two larger, more densely packed regions of bond points. The flat layout of the bond pattern can be further described as follows. A continuous sealing bond consisted of a broken chevron pattern with a width of 0.289 mm to attach the free ends of SMS nonwoven material. The rotary bond pattern had an overall circumference of 38.88144 mm. There was a distance of 6.143 mm in the strand direction (on the fold side) between end cap regions for each set functional bonded areas, where in this 6.143 mm wide region the strands are cut mechanically in the process and allowed to snap back to the anchor end cap bond regions.

The nine angled bands can be further described as an array of 0.011 mm squares (with 0.009 mm tolerance) arranged in a perfectly square grid with a spacing of 0.020 mm (with a tolerance of 0.001 mm). The band is angled at 70 degrees from the axis of strand direction/placement with outer dimensions of the parallelogram being 0.940 mm (in the cross filament direction) by 0.125 mm (in the filament direction).

The two end capping band regions can be further described as solid regions with seven 0.031 mm grooved channels, with a groove depth of 0.015 mm, each of the seven grooved channels is angled at 70 degrees from the axis of filament direction/placement. After grooving, the remaining eight bands have the outer dimensions of the parallelogram being 0.940 mm (in the cross filament direction) by 0.125 mm (in the filament direction). The overall end capped region(s) had the following filament direction dimensions: 1.260 mm width (on the fold side) and tapered to 0.75 mm (on the sealing bond side).

We qualitatively tested the resulting composites by repeatedly stretching them to their maximum stretch. These representative composites of the invention remained intact during the repeated stretching—i.e., each had integrity and was adapted for use as an elastomeric material to be employed in higher-order assemblies.

What is claimed is:

1. A process for making a composite, the process comprising the steps of:
    providing a first substrate;
    treating at least a portion of the first substrate with an adhesive having a softening point lower than the softening point of the first substrate;
    allowing the adhesive to set such that the adhesive is no longer tacky;
    winding the treated first substrate to form a roll;
    thereafter unwinding the treated first substrate;
    inputting energy to the unwound, treated first substrate, thereby activating at least a portion of the adhesive coated on the first substrate, wherein the input of energy is effected before, concurrent to, or after the first substrate is brought into contact with a second substrate;
    providing the second substrate;
    joining at least a portion of the first substrate to at least a portion of the second substrate to form a composite, wherein the first substrate and second substrate are joined at least in part by the activated adhesive.

2. The process of claim 1 wherein not all adhesive is activated.

3. The process of claim 2 wherein the adhesive is activated by ultrasonic energy.

4. The process of claim 3 wherein the adhesive is activated at discrete locations.

5. The process of claim 1 wherein the first substrate, the second substrate, or both are elastomeric.

6. The process of claim 2 wherein the adhesive is activated by heat.

7. The process of claim 6 wherein the adhesive is activated at discrete locations, and wherein the locations are characterized by a pattern.

8. The process of claim 1 wherein the roll of treated substrate is made at a geographic location different from the geographic location where the roll is unwound.

9. The process of claim 1 wherein the adhesive has a softening point between about 60 degrees Celsius and 160 degrees Celsius.

10. The process of claim 2 wherein the adhesive is activated by pressure.

11. The process of claim 10 wherein the adhesive is activated by pressure when the first substrate, the second substrate, or both are traveling at a velocity of at least about 300 feet per minute.

12. The process of claim 5 wherein the first substrate, the second substrate, or both are in a stretched condition when joined.

13. The process of claim 1 wherein the linear velocity of the first substrate and second substrate, after being joined to form the composite, is at least about 300 feet per minute.

14. A process for making a composite, the process comprising the steps of:
  acquiring a first substrate, wherein the first substrate is treated with an adhesive, and wherein the adhesive has been allowed to set so that it is no longer tacky;
  thereafter unwinding the treated first substrate;
  inputting energy to the unwound, treated first substrate, thereby activating at least a portion of the adhesive coated on the first substrate; wherein the input of energy is effected before, concurrent to, or after the first substrate is brought into contact with a second substrate;
  providing the second substrate;
  joining at least a portion of the first substrate to at least a portion of the second substrate to form a composite, wherein the first substrate and second substrate are joined at least in part by the activated adhesive.

15. The process of claim 14 wherein not all adhesive is activated.

16. The process of claim 15 wherein the adhesive is activated by ultrasonic energy.

17. The process of claim 16 wherein the adhesive is activated at discrete locations.

18. The process of claim 14 wherein the first substrate, the second substrate, or both are elastomeric.

19. The process of claim 15 wherein the adhesive is activated by heat.

20. The process of claim 19 wherein the adhesive is activated at discrete locations.

21. The process of claim 14 wherein the roll of treated first substrate is made at a geographic location different from the geographic location where the roll of treated first substrate is unwound.

22. The process of claim 14 wherein the adhesive has a softening point between about 60 degrees Celsius and 160 degrees Celsius.

23. The process of claim 15 wherein the adhesive is activated by pressure.

24. The process of claim 23 wherein the adhesive is activated by pressure when the first substrate, second substrate, or both are traveling at a velocity of at least about 300 feet per minute.

25. The process of claim 18 wherein the first substrate, the second substrate, or both are in a stretched condition when joined.

26. The process of claim 14 wherein the linear velocity of the first substrate and second substrate, after being joined to form the composite, is at least about 300 feet per minute.

27. A process for making a composite, the process comprising the steps of:
  providing a first substrate;
  treating at least a portion of the first substrate with an adhesive having a softening point lower than the softening point of the first substrate;
  allowing the adhesive to set such that the adhesive is no longer tacky;
  inputting energy to the treated first substrate, thereby activating at least a portion of the adhesive coated on the first substrate, wherein the input of energy is effected before, concurrent to, or after the first substrate is brought into contact with a second substrate;
  providing the second substrate;
  joining at least a portion of the first substrate to at least a portion of the second substrate to form a composite, wherein the first substrate and second substrate are joined at least in part by the activated adhesive.

28. The process of claim 27 wherein the adhesive is activated by ultrasonic energy.

29. The process of claim 27 wherein the first substrate, the second substrate, or both are elastomeric.

30. The process of claim 27 wherein the adhesive is activated by pressure when the first substrate, the second substrate, or both are traveling at a velocity of at least about 300 feet per minute.

31. The process of claim 29 wherein the first substrate, the second substrate, or both are in a stretched condition when joined.

32. The process of claim 1, 14, or 27 wherein said first and second substrates are webs, said process further comprising the steps of:
  providing an elastic strand; and
  joining at least a part of the elastic strand to at least a part of said first substrate, said second substrate, or both when said first and second substrate are joined, wherein said elastic strand is in a stretched condition when joined, and wherein said elastic strand is disposed between said first and second substrate when joined.

* * * * *